United States Patent [19]

Ross

[11] 4,153,837
[45] May 8, 1979

[54] OPTICAL GAS ANALYZER

[75] Inventor: Thaddeus C. Ross, Santa Barbara, Calif.

[73] Assignee: ANARAD, Inc., Santa Barbara, Calif.

[21] Appl. No.: 878,215

[22] Filed: Feb. 16, 1978

[51] Int. Cl.$^2$ ............................................ G01N 21/26
[52] U.S. Cl. ..................................... 250/343; 250/346
[58] Field of Search ............... 250/343, 344, 345, 346, 250/341, 373; 356/51, 201, 96, 186

[56] References Cited

U.S. PATENT DOCUMENTS

| | | | |
|---|---|---|---|
| 3,206,597 | 9/1965 | Fertig et al. | 250/343 |
| 3,700,891 | 10/1972 | Luft | 250/343 |

*Primary Examiner*—Davis L. Willis
*Attorney, Agent, or Firm*—W. R. Evans; R. M. Skolnik

[57] ABSTRACT

An optical gas-concentration analyzer which utilizes the infrared absorption principle has a sample chamber and reference chamber with infrared source and detector assemblies spaced at opposite ends of an in alignment with the chambers. An electronic processing system utilizes a spectral-absorption electrical signal from the detector assembly to derive the desired gas-concentration measurement for readout from a display device. Barometric correction means is provided to permit on site calibration by the user of the gas analyzer via an atmospheric pressure calibration indication obtained on the display device by switching the apparatus to a calibrating mode. Apparatus for compensating for broadening of the spectral line of a gas the concentration of which is to be measured by another gas in the sample and for the temperature of the sample gas is also provided.

6 Claims, 4 Drawing Figures

OPTICAL GAS ANALYZER

BACKGROUND OF INVENTION

1. Field of the Invention

The present invention relates to improvements in optical gas analyzers and more particularly, to refinements in non-dispersive infrared analyzers in order to obtain adequate performance for medical and other precision applications.

2. Description of Prior Art

The inventor of the present invention has contributed to the prior art devices in the area of infrared gas analyzers and this prior art as exemplified in U.S. Pat. No. 3,932,754 substantially sets forth one aspect of devices commercially utilized to date for non-medical applications. The inventor in setting forth to perfect instrumentation for medical applications found that the prior art teachings contained in the above referenced patent and others known in the art, lacked the degree of reliability and sophistication necessary for medical applications.

For example, in medical applications such as instrumentation in life support systems in which the output of information is of a critical nature, the necessary degree of calibration and other performance standards, as hereinafter explained in detail, was not available with the prior art equipment. Although the present invention will be particularly discussed with respect to the benefits it provides for medical applications, these same advantages also lend themselves to industrial and other applications as well.

SUMMARY OF THE INVENTION

It is therefore an object of the present invention to provide a highly accurate non-dispersive infrared gas-concentration analyzer ideally suited for medical and other applications.

The non-dispersive analyzer of the present invention has been designed for use in medical gas applications. In this application, the gas analyzer measures the concentration composition of inspired and expired gas to aid in monitoring pulmonary and cardiovascular parameters for clinical and research use. The concentration of carbon dioxide, nitrous oxide and selected halogenated hydrocarbons can be measured on a simultaneous and essentially instantaneous, breath-to-breath basis. Combined analysis of respiratory gas composition leads to a number of useful metabolic and respiratory evaluations that are otherwise unavailable. This of course requires a reliable, high-sensitivity analyzer.

The analyzer of the present invention compares the optical (infrared) transmittance of two optical paths. One optical path passes through a sample cell or chamber of unknown gas concentration and the other optical path passes through a reference cell or chamber. The difference in optical transmittance between these paths is a measure of the concentration of a gas in the sample chamber. The variation in transmittance is sensed by a photon detector and the signal from the detector is processed to drive a display device providing a direct readout of the concentration of the unknown gas.

Barometric correction means is provided to permit on site calibration by the user of the gas analyzer to eliminate the otherwise inevitable errors in readings of about 3% per inch of mercury ambient pressure change which normally result from gas expansion and contraction in the sample chamber. In order to set the barometric correction means accurately, a circuit switches the display device to indicate the precise barometric pressure for which the correction means is set. Inasmuch as the display device is required to provide the readout of gas concentration in the normal operating mode, this switching arrangement elegantly provides for precise calibration without additional precision components.

Certain gases mixed with the gas the concentration of which is to be measured to form the sample gas may slightly affect the concentration readout. To provide extreme accuracy which may be required for medical applications, therefore, an adjustment apparatus for compensating for this effect is also provided. In one embodiment, the adjustment apparatus is calibrated to be set directly to particular combinations of gases in the sample for easy operation.

The temperature of the sample gas in the sample chamber can also affect the analyzer readout. An automatic temperature compensation circuit is therefore provided again to obtain the extreme precision which may be needed in medical applications.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

DESCRIPTION OF THE PREFERRED EMBODIMENTS

Figure 1:
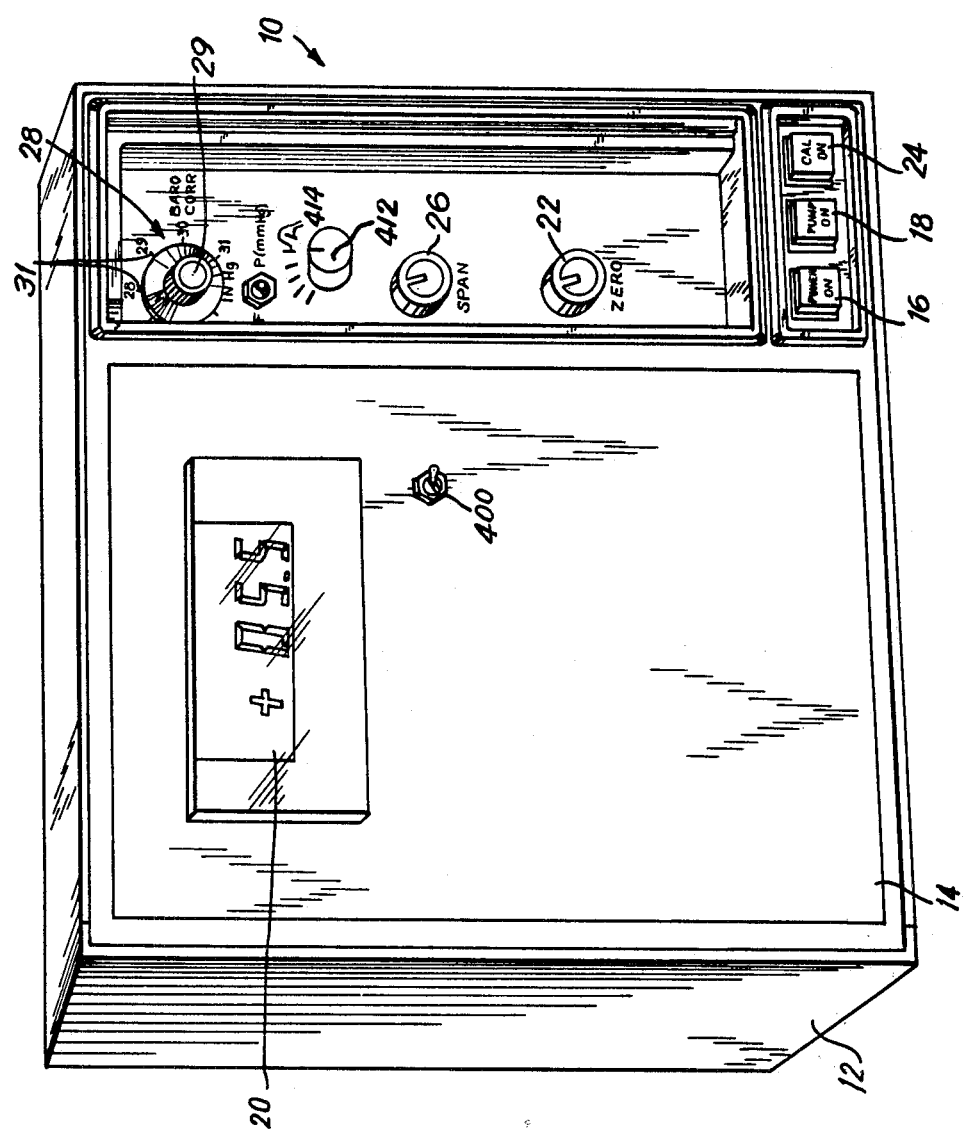
FIG. 1 is a perspective view of a gas analyzer system embodying the present invention.

The gas analyzer 10 illustrated in FIG. 1 may take various shape and forms and contain all or part of the various features of the present invention which are hereinafter discussed in detail. The gas analyzer 10 is employed for various applications and in particular, for medical applications, it may be used for patient monitoring or in an operating room to detect the presence of certain gases.

The gas analyzer 10 is used with a gas pickup (not shown) that receives a sample of the gas to be analyzed. The sample gas is then transmitted through the analyzer 10 in order to provide a readout on display means 20. The gas analyzer 10 may include a cabinet 12 having a front panel 14 containing thereon various controls necessary for the operation of the analyzer 10.

To operate the analyzer 10 the power switch 16 is activated and thereafter the pump switch 18 is energized to activate the pump (not shown) necessary to effect the flow of the sample gas through the analyzer 10.

To check instrument calibration which may be desired occasionally, one may first allow the instrument to draw a known gas composition not containing the gas to be detected, such as clean air, at which time the analyzer 10 should read zero concentration at the display means 20. If other than zero readings appear, the zero control knob 22 would be adjusted to make the display meter read zero. To check the full scale span calibration, the calibration switch 24 is depressed. This actuates the cal wedge mechanism (see FIG. 2) and appropriate scaling resistors in the display device network to effect a full scale indication with a simulated input signal. If the indication is either over or under full scale on the display means 20, the span control 26 is adjusted to show exactly full scale on the display means 20 and this restores the correct calibration to the gain circuits in the analyzer 10.

The barometric correction means 28 including knob 29 and indicating markings 31 on the front of the analyzer will be hereinafter discussed to illustrate the need, particularly in medical applications, for a refinement in the instrumentation not previously available.

OPTICAL UNIT

Figure 2:
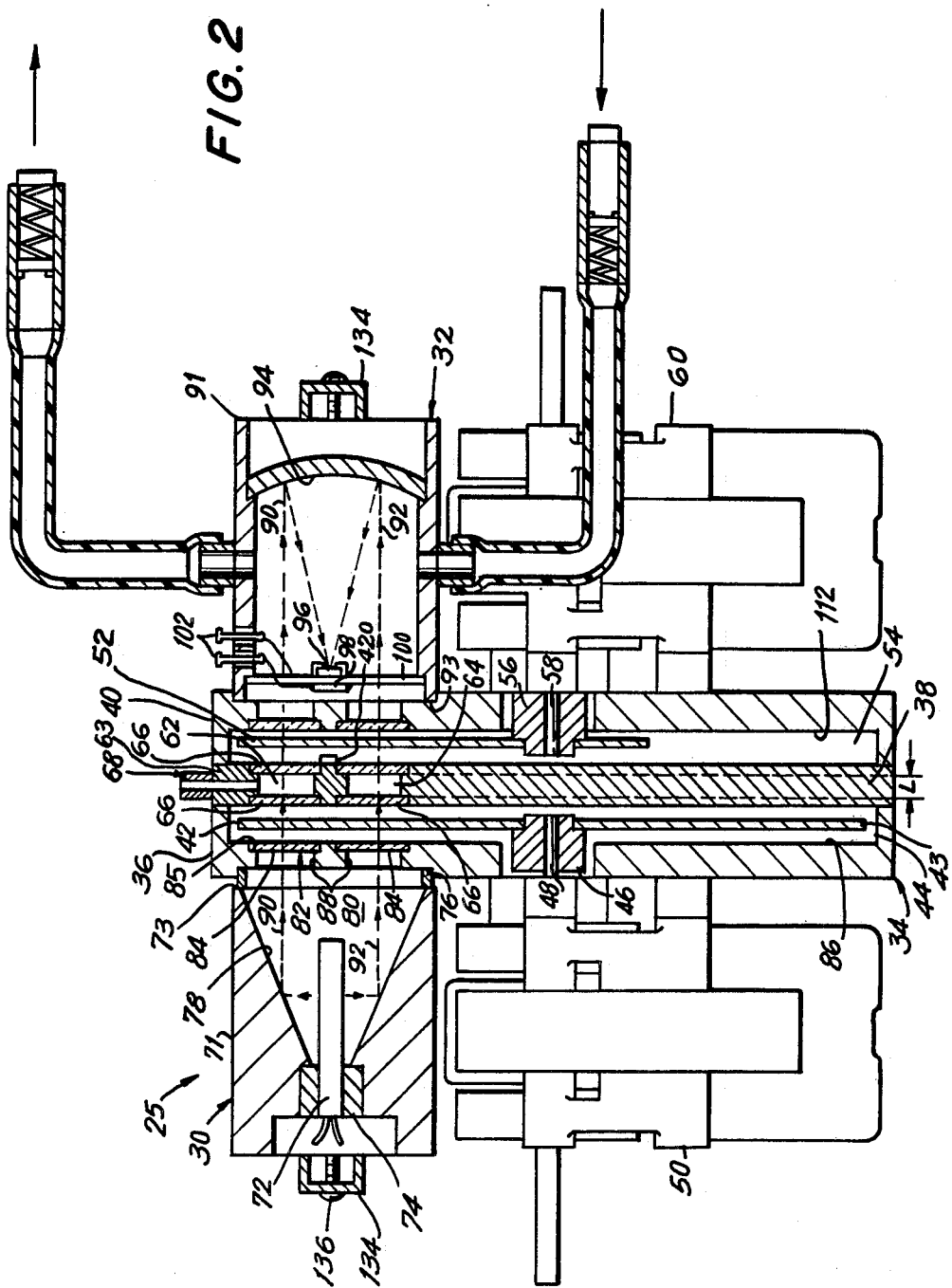
FIG. 2 is a side plan view, partially sectionalized and partially broken away, of the optical assembly portion of the gas analyzer.

Referring now to FIG. 2, the optical unit 25 which is contained within the cabinet 12 of the gas analyzer 10 (FIG. 2) utilizes the infrared absorption principle for determining the quantity of one or more gases in a sample. The gas analyzer optical unit 25 includes as its principal components an infrared projector means or assembly 30 and detector means or assembly 32 in spaced axial alignment therewith. An optical assembly 34 is between the projector assembly 30 and detector assembly 32. It comprises a source end plate 36, a chamber means 38 and a detector end plate 40 all assembled together by fasteners (not shown).

A chopper disc assembly 42 is contained within a cavity 44 of plate 36 and includes a disc 43 mounted on a hub 46 affixed to a shaft 48 of a chopper motor 50 which is mounted on plate 36. The cal wedge assembly 52 is contained within a cavity 54 of plate 40 and mounted on a hub 56 affixed to shaft 58 of cal wedge motor 60 mounted on plate 40.

The chamber means 38 as seen in FIG. 2 is an extruded frame with a sample path or chamber 62 extending axially through a head portion 63 and in spaced relation thereto, a reference path or chamber 64, both chambers having the same dimensions. The chambers may, for example, have diamters in the range of 0.10 inch to 2.0 inches.

The reference chamber 64 and the sample chamber 62 have the same length L which may vary from 0.1 to 30 inches. Each chamber 62 and 64 is sealed at each end by windows 66 that may be epoxied in place and are transparent in the spectral region of the instrument. The sample chamber 62 is provided with an inlet port 68 and a similar outlet port (not shown) to permit the sample gas to flow therethrough. The reference chamber 64 may be filled with ambient air or an inert atmosphere prior to sealing with the windows 66.

The infrared projector means 30 includes a casing 71 with an open front end 73 having an infrared emitting element or source 72 held in place by an insulating bushing 74. The casing 71 is thermally insulated from optical assembly 34 by an annular gasket 76 extending between its front end 73 and the source end plate 36. The inside surface 78 of the infrared projector means 30 has a highly reflective conical shape defining cavity 80. The air space in cavity 80 defined by the interior conical surface 78 is protected from buffeting by air currents by baffle means 82. The baffle means 82 is seen to include a pair of baffle plates 84 that are disposed in seats 85 provided on the inner wall 86 of the source end plate 36 and in alignment with the sample chamber 62 and reference chamber 64. The baffle means 82 is essential to reducing to a minimum the optical noise which is generated by the infrared emitter 72.

The oblong shaped infrared emitting source 72 has essentially blackbody radiation characteristics and emits from its total surface omnidirectionally. The conical reflecting surface 78 reflects those beams or rays 90 and 92 (only one of each shown) which are at appropriate angles with the reflecting surface 78 along an optical path to the detector assembly 32 through the chambers 62 and 64, respectively, as shown. Beams 90 thus pass through the sample chamber 62 and beams 92 thus pass through the reference chamber 64.

The detector assembly 32 includes a housing 91 with an open front end 93 and a beam-collecting, concavely shaped mirror 94 at the rear of the housing 91 facing the front end 93. A spectral filter 96 is positioned in the housing with an adjacent detector element 98 on a supporting member 100 to collect and detect the beams 90 and 92. Lead-in wires from the detector 98 are terminated on connector terminals 102. Terminals 102 are in turn connected to the preamplifier 202 of the circuit of FIG. 3.

Clamps 134 are provided at the end of the projector assembly 30 and detector assembly 32 to mechanically retain the projector and detector assemblies respectively with fasteners 136 as seen in FIG. 2 that are connected to the detector end plate 40 and source end plate 36. The detector element 98 is photoelectrical, but may vary in particular design for best response to the spectrum of the particular gas under study. The emitting source 72 may have a infrared or other bandwave spectrum.

ELECTRONIC PROCESSING SYSTEM

The electronic processing system generally identified at 200 (FIG. 3) amplifies the signal from the radiation detector 98 and further operates on this signal to extract the information of the detector signal. The system aims to optimize the utilization of the detector signal to attain the highest signal-to-noise ratio in the output of the instrument to maximize the sensitivity of readings of small concentrations of gases.

The gas concentration signal waveform developed by the photoelectric detector 98 is interrupted or chopped in correspondence with the optical signal incident on the detector. The optical signal incident on the detector is shaped by the action of the chopper disc 43 which is rotatingly interposed between the infrared source 30 and the detector assembly 32.

FIG. 2 shows the chopper disc 43 interposed between the infrared source assembly 30 and the infrared detector assembly 32. Disc 43 is circular with three circumferentially spaced arcuate slots (not shown) aligned with each of the sample and reference gas chambers 62, 64. The disc portions between slots then periodically interrupt the optical path from source assembly 30 to detector assembly 32 to chop the transmitted rays 90, 92 and the resulting signal from detector 98. The slots aligned with the respective chambers 62, 64 are in radially alternate sections of the disc 43 so that the rays 90, 92 alternate. The chopped signal pulses from the detector 98 thus alternately correspond to the spectral absorption of the sample and reference chamber gases.

Figure 3:
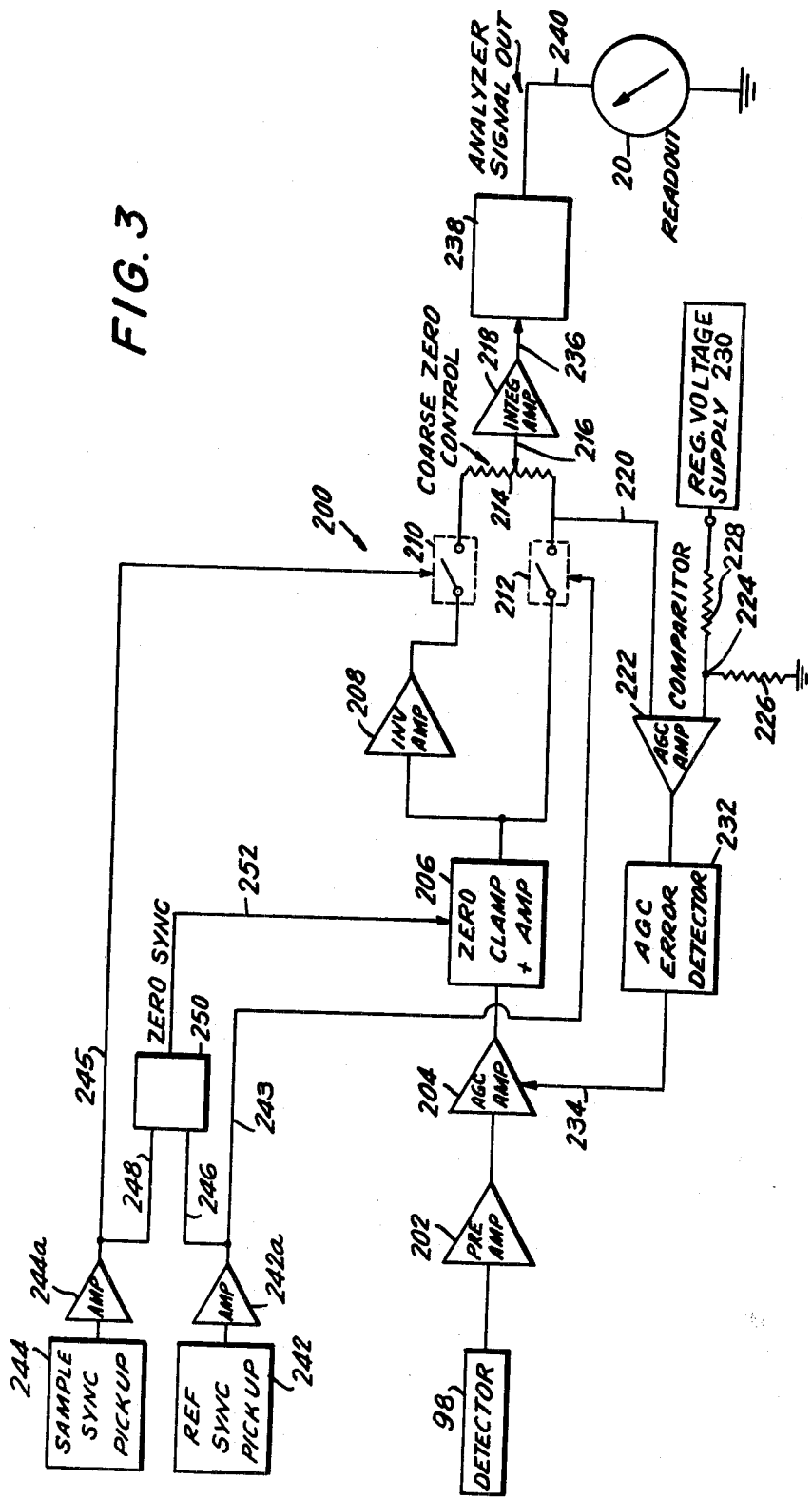
FIG. 3 is a diagram generally illustrating the circuit of the gas analyzer.

A reference synch signal corresponding to the zero level pulse signals at the transition from rotationally positioning a slot in alignment with one chamber, for example the sample chamber, and then the other is also provided by a pick up 242 (FIG. 3). The pick-up may be a photo electric device which receives light from reflective markings spaced about the disc 42 in radial alignment with the slot transitions as described in the parent application or other known synchronizing device. A similar sample synch pick-up 244 (FIG. 3) indicates the end of each slot ahead, in phase, of the reference synch signal to define, in combination, a zero synch interval between each sample and reference signal pulse.

The alternate signals are integrated and compared in the electronic system 200 to develop a DC difference level signal indicating the difference in concentration of the gas in the reference chamber 64 from the concentration of the same gas in the sample chamber 62. The concentration of the gas in the reference chamber is known so that the resulting signal is calibrated to indicate the concentration of the gas in the sample on the display 20 (FIG. 1).

In medical applications, the sample gas concentration information is of critical importance to the health condition of a patient and/or the physician. For example, the level of various gases such as $N_2O$ which is used by anesthesiologists during operations supplied to a patient is critical to the patient and the level of the same gases which escape into the operating room can be critical to the physician and staff. By way of example, if the patient is in infant, then the sample specimen available on which the calculations are to be performed are of minimal volume, sometimes as small as 0.2 cc. The inventor found that the teachings of the prior art did not permit the degree of reliability necessary to make use of such small samples and to process them through a gas analyzer with sufficient accuracy.

In order to provide a more refined instrument, the sampling or chopping rate must be adequately high to provide a sufficient number of signal pulses per unit time to yield the desired overall instrument response speed and accuracy. In the interest of maximizing detector signal-to-noise ratio, it is desirable to chop the infrared energy beams incident on the detector at the highest rate practically attainable. Towards this end, the chopper disc 42 (FIG. 2) is provided with the three sets of slots (not shown) for each optical path so as to give three complete chopping cycles of alternate sample and reference gas pulses per motor shaft revolution and the motor is operated at a high rotational speed of, for example, 3300 rpm. In addition, special efforts have been made to attain the fullest possible utilization of the detector signal by extending the measurement process over 100% of its duration including sloping pulse edges instead of only a central steady state region as previously generally employed. Extending the measurement time narrows the noise bandwidth in correspondence to the increase in signal integration time. The noise signal $E_n$ generated by a resistive element of R ohms at a temperature T degrees Kelvin is expressed by the known equation $E_n = (AKTdFR)^{\frac{1}{2}}$ where dF is the noise bandwidth of the signal and K is Boltzmann's constant. By decreasing the noise bandwidth dF, the resistive element noise voltage is seen to be proportionately decreased.

In FIG. 3, the signal developed by the detector 98 is amplified by a conventional integrated circuit preamplifier 202 to a working signal level of approximately 1 volt. This signal is then coupled to an additional automatic gain control (AGC) amplifier stage 204 having a gain adjustment by an electronic control signal applied via lead 234 from external sources comprising another automatic gain control element 222 and detector 232. The output signal of the AGC amplifier 204 is clamped to ground at appropriate points in the waveform corresponding to the zero sync interval by a conventional zero clamp circuit 206 to establish an initial ground reference for each chopped signal pulse to be processed.

The output signal from zero clamping circuit 206 is divided into two voltage paths; one signal path couples the clamping circuit signal through an inverting amplifier 208 to a conventional signal switching circit 210, and the other path couples the signal directly to another conventional signal switching circuit 212. The outputs from the switching circuits 210 and 212 are connected respectively to the opposite ends of a potentiometer 214 having a center arm 216 which can be positioned to balance the effect of the signals applied at the ends thereof.

Switching circuit 210 is actuated by the sample sync pick up 244 via amplifier 244a and lead 245. Switching circuit 212 is actuated by the reference sync pick up 242 via amplifier 242a and lead 243. As a result of this circuit configuration, the sample gas signal inverted by the action of inverting amplifier 208 and the reference gas signal appear at potentiometer arm 216 sequentially. A portion of the output of switching element 212 (the reference gas signal) is coupled, via line 220, to AGC amplifier 222 which compares the amplitude of the reference gas signal to a preset voltage appearing at the junction 224 of a resistor divider network formed by resistors 226 and 228. Resistor 226 is connected to ground and resistor 228 is connected to a regulated voltage supply 230. The output signal of AGC amplifier 222 is coupled to the AGC error detector 232 which develops a control voltage for the AGC amplifier 204 in the proper amplitude and polarity as to effect amplitude stabilization of the reference gas pulse.

The potentiometer arm 216 is coupled to an integrator 218 where the signal is integrated and filtered to yield an average DC voltage. This voltage is coupled via lead 236, scaler 238 which may take the form of amplifiers, resistive divider networks, linearizer networks, etc. and lead 240 to the readout display device 20 such as a conventional digital voltmeter, a chart recorder or a combination of any such or similar devices.

As shown in FIG. 3, the reference sync pickup 242 and amplifier 242a, and the sample synch pickup 244 and amplifier 244a are coupled via respective leads 246 and 248 to a logic gate 250 which yields a zero synch signal corresponding to the zero synch interval between each sample and reference gas signal. This zero synch signal is coupled, via lead 252, to control the zero clamp circuit to assure a zero transition between successive gas signal pulses. The timing relationship defined by the zero transition between successive pulses permits the integration process carried out in the integrator 218 to utilize the full duration of the detector 98 signal by extending the integration time to approximately 100% of signal duration. This affords the maximum amount of time over which to average and smooth out the constantly, but minutely varying impulse contributions of the sample gas. Thus, the disclosed circuitry provides a substantially constant output voltage regardless of minute input signal variations.

BAROMETRIC CORRECTION SYSTEM

As described, the gas analyzer measures the absorption of the rays 90, 92 to determine the gas concentration in the sample chamber. The absorption, however, is related to the number of gas molecules in the chambers. Termperature and pressure affect the number of molecules present in a given space such as the chambers in accordance with the well known Charles-Boyle gas law $PV=nRT$. Inasmuch as the temperature stabilizes, it will be disregarded as a variant in this discussion. It remains necessary, however, to compensate for pressure changes because, although the pressure in the sealed reference chamber is fixed (at the stabilized temperature) and thus can be compensated for in the fixed design elements of the analyzer, the pressure in the sample chamber can change through the sample gas inlet 68 (FIG. 2) and similar outlet (not shown). For analyzing the gas in an operating room, for example, the inlet is connected through the pump (not shown) to atmosphere so that the pressure in the sample chamber varies with atmospheric pressure. Atmospheric pressure changes occur as a result of weather conditions and physical location of the equipment and can be monitored on standard weather barometers in the known manner. To get precise measurements from the analyzer, these changes need to be taken into account to reduce the pressure-induced measurement error which otherwise would occur to acceptably low limits.

As described in a prior patent, the inventor has provided the barometric correction means 28 that may be easily and quickly set wherever the analyzer is used simply by operating the calibrated dial 29 on the front panel 14 of the unit 10 shown in FIG. 1.

Figure 4:
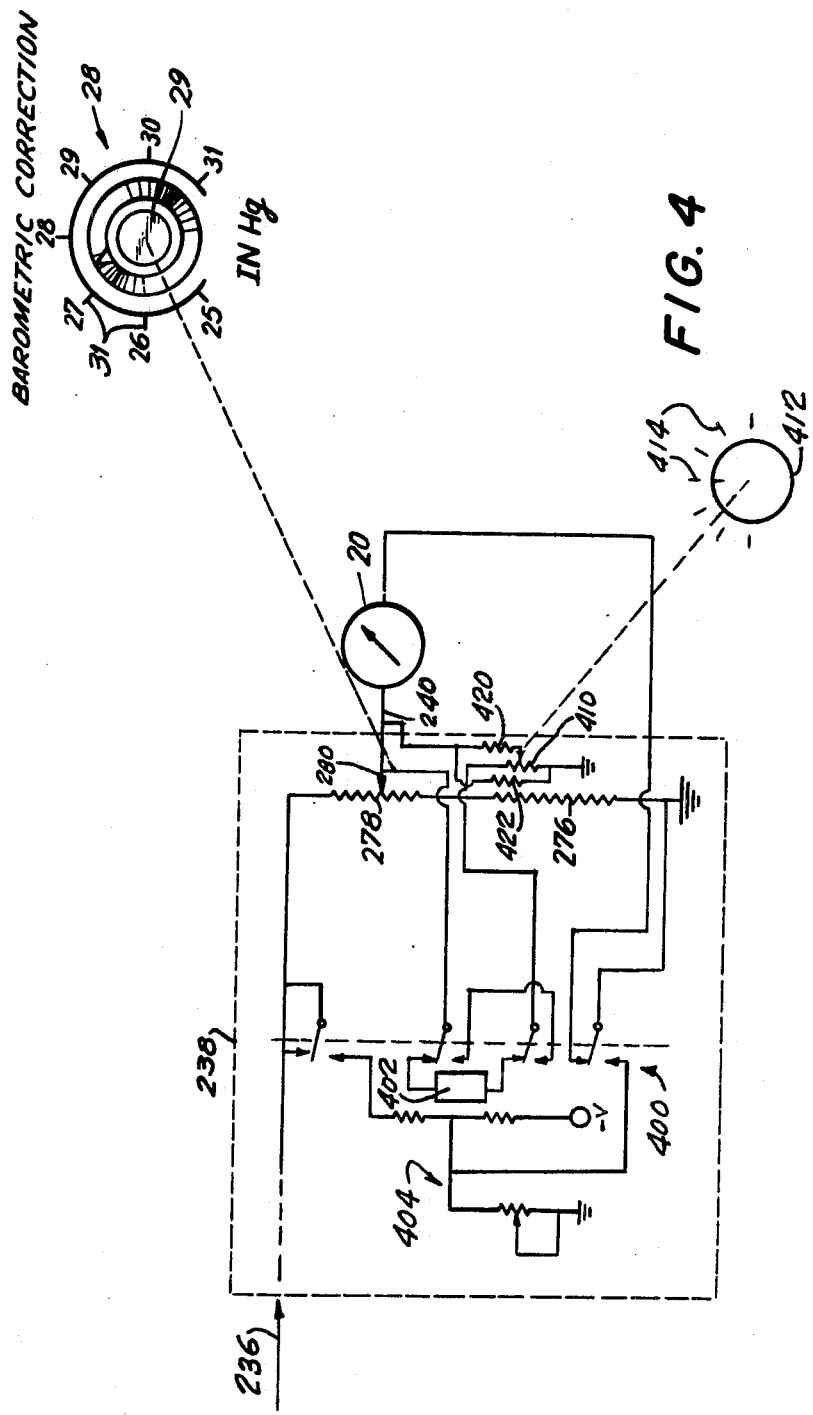
FIG. 4 is a diagram generally illustrating the circuit of a barometric correction structure as it relates to the gas analyzer.

As in the prior patent, the circuit for barometric correction in the scaler 238 as shown in FIG. 4 includes a voltage divider network of a serially connected fixed resistor 276 and potentiometer 278 connected between ground and the input lead 236. The movable arm 280 of the potentiometer picks off a pressure-compensating fraction of the potentiometer signal for connection to the readout display device 20. The dial 29 mechanically moves the arm 280 and is calibrated in barometric pressure units corresponding to the pressure compensation of the potentiometer. The user therefore consults a standard barometer to determine the atmospheric pressure, and correspondingly sets the control dial or knob 29 and thus the arm 280 of the potentiometer. This scales the signal applied to the readout display device 20 to compensate for gas expansion or compression in the sample chamber due to the atmospheric pressure.

The inventor has now found, however, that even the most careful setting of dial 29 cannot produce a repeatability better than about ¼ inch mercury because of the relative coarseness of even fine calibration markings 31 for the dial 29. Further preciseness could thus be obtained from the analyzer if the pressure compensation were made more precise.

Although a variety of costly electro-mechanical calibration devices such as verniers and decade scaling switches are known to give more precise settings, the inventor elegantly incorporated the pre-existing display device which is obviously essential to any analyzer into an improved pressure calibration system to save the expense of such costly, known precision calibration devices. He provided a ganged, four pole switch 400 (FIG. 1 and 4) which switches the display device from the normal operating mode previously described in which it provides a readout of the concentration of a gas in the sample gas to a calibration mode in which the display device provides a precise pressure reading. The calibration mode is particularly effective when the display device 20 is a digital display as shown in FIG. 1 to provide a precise digital readout of the pressure to as many decimals as needed to maintain the significance of the least significant digit in the gas-analysis readout of the operating mode, for example a millimeter of mercury.

As shown in FIG. 4, the switch 400 switches the display device 20 from connection to lead 236 through pressure-compensating potentiometer 278, as pre-set by dial 29, and scaler 402 which scales the signal to the display device 20 to indicate gas concentration to connection to scaler 404 which scales a signal from a potential (power) source $-V$ to indicate pressure as adjusted by the retained series connection of the potentiometer 278. The potentiometer is now set by dial 29 to indicate pressure on the display and thus pre-set the pressure compensation when the switch 400 is returned to the operating mode. Scaler 404 is shown in FIG. 4 as being of a known resistive network type. The user thus first sets switch 400 to indicate pressure on the display device 20 and adjusts dial 29 until the barometric pressure is indicated on the display (along with the zero and full scale calibrations previously described) and then throws switch 400 to indicate gas concentration on the display device. Inasmuch as the setting of potentiometer 278 via dial 29 remains unchanged and the potentiometer is in both the pressure and operating mode circuit arrangements, precise pressure calibration of the analyzer is obtained.

CORRECTION FOR BROAD SPECTRUM

The inventor has also now discovered that some gases mixed with a specimen gas the concentration of which is to be measured affect the concentration measurement of the analyzer. In many medical applications, for example, the sample gas in a mixture of one or more carrier gases and the specimen gas the concentration of which in the carrier is to be measured. In specific example, knowing the concentration of carbon dioxide ($CO_2$) in a patient's breath may be medically desired when the patient is breathing either air which is largely nitrogen ($N_2$) or pure oxygen ($O_2$). The inventor has found that the analyzer indicates slightly different concentrations of $CO_2$ in an $N_2$ carrier than in an $O_2$ carrier when the actual concentration of $CO_2$ is the same. Correction of this problem is thus clearly desirable to still further improve the accuracy of the analyzer.

The inventor attributes this carrier-gas variation to a broadening of the spectral line of the specimen gas produced by the infrared ray when it passes through the sample gas (carrier and specimen mixture) in chamber 62 which broadening, because it coincides with the spectral line of the specimen gas to be measured, cannot be removed by the masking of other spectral lines from the carrier gas as described in the parent application. The increased photons of the broadened spectral line increase the signal from the detector 98 (FIG. 2) and thus the concentration reading of the analyzer over that which it would have been without the spectral broadening from the carrier gas. The spectral line broadening phenomenon is explained by a collision mechanism between the molecules of the specimen gas to be measured and those of certain carrier gases which interact with the particular specimen gas. For example, an $N_2$ carrier (air) broadens the spectral line of $CO_2$.

Having now identified the problem, it can be corrected by adjusting the analyzer processing system signal gain to the display device 20 with a potentiometer 410 series connected between the signal processing system and the display device as shown in FIG. 4. The potentiometer is adjusted by a knob 412 (FIGS. 1 and 4) with associated index marks 414. The index marks may be either numerical for setting to a particular predetermined numeral at which the potentiometer 410 is dimensioned to compensate for the spectral broadening of a particular carrier and specimen sample gas mixture, or may be designated directly with particular sample gas combinations, e.g. $N_2:CO_2$ and $O_2:CO_2$, to adjust the potentiometer 410 for the spectral broadening of the different sample gas mixtures directly. Further sophistication can be provided by adding a second, series analyzer gain potentiometer (not shown) to potentiometer 410 to compensate not only for the particular mixture of particular specimen and carrier gases, but also for the concentration of a particular gas in the carrier, e.g. $N_2$ in air, which may differently affect spectral broadening of the specimen gas the concentration of which is to be measured.

Inasmuch as the adjustment for spectrum broadening is in the output of scaler 238, it is necessary in this embodiment to adjust the spectrum-broadening correction potentiometer 410 before the pressure-compensation potentiometer 278 to avoid changing the pressure compensation with a later spectrum broadening correction. If this is not desired, the spectrum broadening correction circuit, and next to be described temperature correction circuit, can be moved to the other side of switch 400 so as to affect only the gas-concentration signal in the operating mode.

TEMPERATURE CORRECTION

As already described, temperature as well as pressure affects the molecular density and thus the spectral absorption of the sample gas. Temperature-induced changes in spectral absorption change the signal to the detector 98 (FIG. 2) and thus the analyzer readout on the display device 20. Inasmuch as the sample gas which is analyzed is in the chamber 62 (FIG. 2) inside the optical assembly 34 (FIG. 2) which is inside the cabinet 12 (FIG. 1), the structure of the analyzer insulates the sample chamber 62 from moderate changes in ambient temperature such as changes in room temperature. The temperature of the sample chamber then stabilizes at a temperature which may be somewhat higher than ambient because of heat from various analyzer components such as chopper motor 50 (FIG. 2) and resistor 276 (FIG. 4). The analyzer can then be designed for the molecular density of the sample gas at the stable temperature.

When the analyzer is exposed to extremes of ambient temperature as in arctic or tropical environments, however, the temperature of the sample chamber may significantly change and the set design compensation for temperature becomes ineffective. To make the analyzer useful in such extreme environments, therefore, a thermistor, or other temperature responsive electrical element 420 and resistor 422 are arranged in a potential dividing network connected to the lead 240 to the display 20 as shown in FIG. 4. The thermistor 420 is in thermal communication with the gas in the chamber 62 by mounting it adjacent the chamber as shown in FIG. 2. The resistive network of thermistor 420 and resistor 422 is then dimensioned to adjust the signal to the display device 20 to compensate for temperature changes in the sample gas as indicated by the temperature of the chamber.

CONCLUSION

Although illustrative embodiments of the invention have been described in detail herein with reference to the accompanying drawings, it is to be understood that the invention is not limited to those precise embodiments, and that various changes and modifications may be effected therein without departing from the scope or spirit of the invention.

I claim:

1. In a gas concentration analyzer having a chamber for a sample gas to be analyzed in which the pressure of the sample gas is affected by atmospheric pressure, optical means for producing a spectral line generally proportional to the concentration of a gas in the sample but affected by the pressure of the sample gas in the chamber, detector means for converting the spectral line into a corresponding electrical signal, signal processing system means for processing the electrical signal into a signal indicating the concentration of the gas in the sample gas, a display device normally connected to the signal processing means for normally displaying the concentration-indicating signal as a readout of the gas concentration, and barometric correction means connected to the display device for adjusting the readout to compensate for the effect of the atmospheric pressure; an improved pressure calibration apparatus comprising:
   a power supply;
   a scaler for scaling power from the supply to indicate atmospheric pressure on the display device; and
   a switch for switching the display device from the normal connection to the signal processing system means for displaying the gas concentration to connection to the scaler while retaining the connection of the barometric correction means to the display device for now calibrating the barometric correction means precisely to the atmospheric pressure with the pressure then indicated on the display device.

2. Apparatus as in claim 1; wherein the barometric correction means is normally connected in series between the signal processing means and the display device and the switch switches the barometric correction means into series between the scaler and the display device.

3. In a gas concentration analyzer having optical means for producing a spectral line generally proportional to the concentration of a specimen gas in one or more carrier gases at least one of which carrier gases broadens the spectral line of the specimen gas, detector means for converting the spectral line into a corresponding electrical signal, signal processing system means for processing the electrical signal into a signal indicating the concentration of the specimen gas in the carrier gases, and a display device for displaying the concentration-indicating signal as a readout of the specimen gas concentration; correction apparatus for the spectral broadening of the carrier gases, comprising:
   correcting means connected between the signal processing system means and the display device for adjusting the gain to the display device to compensate for the spectral broadening by the carrier gases of the spectral line of the specimen gas.

4. Apparatus as in claim 3; and additionally comprising adjusting means for adjusting the correcting means and index means associated with the adjusting means and designated in particular carrier and specimen gas combinations for directly indexing the adjusting means to set the correcting means to compensate for the particular gas combination.

5. In a gas concentration analyzer having a chamber for a sample gas to be analyzed the temperature of which sample gas may vary, optical means for producing a spectral line generally proportional to the concentration of a gas in the sample gas but affected by the temperature of the sample gas, detector and signal processing system means for converting the spectral line into an electrical signal indicating the concentration of the gas in the sample gas, and a display device connected to the detector and signal processing system means for displaying the concentration-indicating signal as a readout of the gas concentration; temperature compensation means, comprising:

temperature resonsive electrical element means in thermal communication with the sample gas in the chamber and electrically connected to the display device for correcting the gas-concentration readout to compensate for the effect of the temperature of the gas.

6. Apparatus as in claim 5 wherein the temperature responsive means is a thermistor on the chamber for the thermal communication with the gas and electrically connected in a resistive network which is between the detector and signal processing system means and the display device.

* * * * *